United States Patent [19]

Cook et al.

[11] Patent Number: 4,774,236

[45] Date of Patent: Sep. 27, 1988

[54] 17α-(SUBSTITUTED-METHYL)-17β-HYDROXY/ESTERIFIED HYDROXY STEROIDS AND PHARMACEUTICAL COMPOSITIONS CONTAINING THEM

[75] Inventors: C. Edgar Cook; C. Ray Tallent; Jerry R. Reel; Mansukh C. Wani, all of Research Triangle Park, N.C.

[73] Assignee: Research Triangle Institute, Research Triangle Park, N.C.

[21] Appl. No.: 908,288

[22] Filed: Sep. 17, 1986

[51] Int. Cl.[4] ...................... A61K 31/58; A61K 31/56; C07J 1/00; C07J 43/00

[52] U.S. Cl. .................................... 514/176; 514/179; 260/397.45; 540/94; 540/95; 540/107; 540/108

[58] Field of Search ............................... 514/176, 179; 260/397.45; 540/94, 95, 107, 108

[56] References Cited

U.S. PATENT DOCUMENTS

| | | | |
|---|---|---|---|
| 4,233,296 | 11/1980 | Teutsch et al. | 514/172 |
| 4,447,424 | 5/1984 | Teutsch et al. | 514/179 |
| 4,536,401 | 8/1985 | Neef et al. | 514/173 |
| 4,540,686 | 9/1985 | Philibert et al. | 514/179 |

FOREIGN PATENT DOCUMENTS

| | | |
|---|---|---|
| 0192598 | 8/1986 | European Pat. Off. . |
| 3506785 | 7/1986 | Fed. Rep. of Germany . |

OTHER PUBLICATIONS

Chemical Abstracts; vol. 103 (1985); #6617y; Neef et al. Chemical Abstracts, Issue 1, (1988), #6285s; Philibert et al.

*Primary Examiner*—Leonard Schenkman
*Assistant Examiner*—Joseph A. Lipovsky
*Attorney, Agent, or Firm*—Oblon, Fisher, Spivak, McClelland & Maier

[57] ABSTRACT

Steroids of the formula:

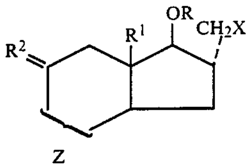

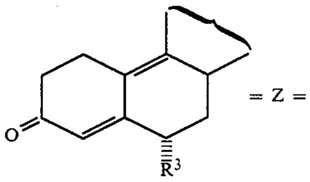

(III)

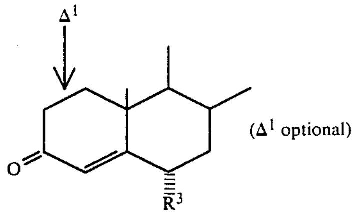

(IV)

which are characterized by a 17α-cyanomethyl, azidomethyl, methoxymethyl, phenylmethyl, or ethynylmethyl substituent and a 17β-hydroxy/esterified hydroxy substituent. The steroids of this invention have glucocorticoid, anti-glucocorticoid, progestational, or anti-progestational activity, depending on the particular structure.

17 Claims, 2 Drawing Sheets

(I)

(II)

(III)

= Z =

(IV)

($\Delta^1$ OPTIONAL)

(V)

(VI) ($R^1$ = Me or Et)

(VII) ($R^1$ = Me or Et)

(VIII) ($R^2$ = α-H, β-OH)

(IX) ($R^2$ = α-H, β-OH)

(X) ($R^2$ = α-H, β-OH)

(XI)

(XII)

(XIII)

(XIV)

17α-(SUBSTITUTED-METHYL)-17β-HYDROXY/ESTERIFIED HYDROXY STEROIDS AND PHARMACEUTICAL COMPOSITIONS CONTAINING THEM

BACKGROUND OF THE INVENTION

1. Field of the Invention

The present invention relates generally to the field of steroids, and in particular, to 17α-(substituted-methyl) steroids represented by partial formula (II), wherein Z is selected from residues represented by partial formulas (III) and (IV), which structures possess a variety of valuable biological properties including glucocorticoid and anti-glucocorticoid, progestational and anti-progestational activities. The invention is also directed to pharmaceutical compositions containing the steroids disclosed in this invention.

2. Description of the Background Art

M. Hübner, K. Ponsold, M. Oettel and R. Freund, [*Arzneim.-Forsch, Drug Res.* 30:401–406 (1980)] described the preparation of 17β-hydroxy-17α-(substituted-methyl) derivatives of estra-4,9-dien- 3-one (I; R=H, $R^1$=Me) and gona-4,9-dien-3-one (I; R=Me, $R^1$=Et) in which the substituents were:

$R^1$=Me; X=$N_3$, CN, Br, Cl $R^1$=Et; X=$N_3$.

These structures were characterized as progestational agents. In particular, when R=H, $R^1$=Me and X=CN, the steroid designated STS 557 was obtained which had ten times the oral potency of levonorgestrel as a gestagen (M. Hübner and K. Ponsold, *Exper. Clin. Endocrinol.* 81:109–114 [1983]). Incubation of STS 557 with female rat liver microsomes led to isolaion, inter alia, of the metabolite 17α-cyanomethyl-11β,17β-dihydroxyestra-4,9-dien-3-one (II; R=H, $R^1$=Me, $R^2$=α-H,β-OH, Z=III, $R^3$=H) but no biological activity was reported for this product (*Exper. Clin. Endocrinol.* 81: 168–174 [1983]). This product is excluded from the claims of this invention.

In Eur. Pat. Appln. E.P.129,499 (1984), G. Neef, G. Sauer, R. Wiechert, S. Beie, D. Henderson and R. Rohde describe steroids of type (V) wherein the substituted-methyl group at C17 is introduced via 17-oxo intermediates. The compounds of that invention are characterized by a 13α-methyl substituent and thus fall outside the present claims which require a 13β substituent.

In U.S. Pat. No. 4,447,424 to J. G. Teutsch, D. Philibert and R. Deraedt are disclosed steroids of structure (II) wherein the substituents are as follows:

| R | $R^1$ | $R^2$ [α-H,β= | X |
|---|---|---|---|
| H | Me | $.C_6H_4s(CH_2)_2N<$ | CN |
| H | Me | $.C_6H_4—N<$ | $CH_2C≡CH$ |
| H | Me | $.C_6H_4C_6H_4—N<$ | $CH_2C≡CH$ |
| H | Me | $.C_6H_4OCH_2CH_2N<$ | $CH_2C≡CH$ |
| H | Me | $.C_6H_4SCH_2CH_2N<$ | $CH_2C≡CH$ |
| H | Me | $.C_{10}H_6N<$ | $CH_2C≡CH$ |

and Z=(III); where $R^3$=H. These structures are claimed to have anti-glucocorticoid properties. They are excluded from the claims of the present invention.

U.S. Pat. No. 3,906,096 to Bucourt et al is directed to steroidal compounds which have anti-androgenic and anti-estrogenic activities. The compounds of Bucourt et al are different from the present compounds in that the former have an alkoxy group at the 11 position. Further, the compounds of Bucourt et al do not include the $\Delta^{4,9}$ series of compounds as in this invention, nor does the reference disclose a 17α substituent containing a hetero atom.

U.S. Pat. No. 4,540,686 to Philibert et al discloses compounds having anti-glucocorticoid activity. This reference does not disclose 17α substituents containing a hetero atom such as azidomethyl or methoxymethyl.

U.S. Pat. No. 4,547,493 to Teutsch et al is directed to steroidal compounds which have anti-glucocorticoid activity. The $\Delta^{4,9}$ steroids of Teutsch et al require a substituent other than hydrogen at the 2 position of the steroid ring system, and therefore the compounds of the reference fall outside of the scope of the present claims.

U.S. Pat. No. 4,233,296 to Teutsch et al is directed to 11β-substituted-$\Delta^{4,9}$-estradienes having progestomimetic activity. The only 17β substituted methyl substituent is a 2-propynyl group.

Although a large group of steroidal compounds with biological activity is known, as evidenced by the above-described disclosures, there remains a need to discover new and more effective steroidal compounds possessing biological activity, particularly glucocorticoid/anti-glucocorticoid or progestational/anti-progestational activity.

SUMMARY OF THE INVENTION

Accordingly, it is an object of the present invention to provide novel steroidal compounds possessing glucocorticoid activity;

It is another object of the present invention to provide novel steroidal compounds having anti-glucocorticoid activity;

It is yet another object of the present invention to provide steroidal compounds having progestational activity;

It is yet another object of the invention to provide novel steroidal compounds having anti-progestational activity.

These and other objects of the invention as will hereinafter become more apparent have been accomplished by providing novel 11β-substituted derivatives of 17α-(substituted-methyl) steroids (II) wherein Z is selected from partial structures (III) and (IV), which compounds possess binding affinities to glucocorticoid and to progestational receptors. By virtue of such binding, these compounds possess biological activities in warm-blooded animals. The biological activities are glucocorticoid, anti-glucocorticoid, progestational or anti-progestational activities. This surprising range of biological activities of the products of the present invention stems from overlap in the structural requirements for binding to glucocorticoid and progesterone receptors, and represents an important feature of the present invention.

This invention provides for the first time novel

17α-Cyanomethyl- (II; X=CN),

17α-Azidomethyl- (II; X=$N_3$),

17α-Thiocyanomethyl (II; X=SCN),

17α-Methoxymethyl (II; X=OMe), and

17α-Phenylmethyl(benzyl) (II; X=Ph)

derivatives of (II) wherein Z is selcted from partial structures (III) and (IV). In addition it provides for the first time novel 17α-Ethynylmethyl (II; X=$CH_2C≡CH$)

derivatives of (III) providing the substituent $R^2$ does not contain N or S in the molecule. Of these, the 17α- cyanomethyl, 17α-azidomethyl and 17α-methoxymethyl derivatives are preferred. Functional equivalents of these 17α substituents, such as phenyl substituted by $C_1$–$C_3$ alkyl, and substituted methoxy (e.g., $CF_3O$—) or ethoxy are also within the scope of this invention, provided they retain the desired activity.

In its broadest embodiment, the present invention covers the above generalized structures, wherein:

R is H, acyl ($C_1$–$C_{10}$), lower alkyl ($C_1$–$C_3$);

$R_1$ is methyl or ethyl;

$R^3$ is H or methyl; and $R^2$ is selected from the group consisting of oxo, 11α-hydrogen, 11β-

—OH, except when X=CN and R is H

-lower alkyl ($C_1$–$C_{10}$);

-lower alkenyl ($C_1$–$C_{10}$), with the understanding that when C=1, the alkenyl group is methylene and is attached directly to position $C_{11}$;

-lower alkynyl ($C_1$–$C_{10}$);

—$C_6H_5$ and —$C_6H_4.R^4$;

—$(CH_2)n.R^5$ wherein n is 1 to 4;

-pyridyl;

-thiazolyl;

-piperidinyl;

wherein $R^4$ is selected from the group consisting of

—H, 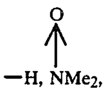 —$NMe_2$,

—$OCH_2CH_2NMe_2(Et_2)$;

-lower alkyl ($C_1$–$C_3$);

—O-lower alkyl ($C_1$–$C_3$);

-halogen;

—$CF_3$;

—$C_6H_5$;

—S-lower alkyl or -phenyl; and $R^5$ is selected from the group consisting of—$NMe_2$-,—$NEt_2$,

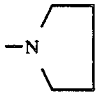, 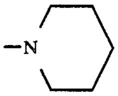, 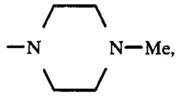,

OMe.

The receptor-binding affinities and biological properties of the foregoing class of steroids fall generally into 4 main groups:

Group I. Compounds in this group have binding affinity for the glucocorticoid receptor and generally possess glucocorticoid, and in particular, topical glucocorticoid activity. These structures (II) wherein Z is selected from partial structures (III) or (IV) are characterized by substituents selected from the following:

R is H or lower acyl and in particular acetyl, propionyl, and butyryl;

$R^1$ is methyl;

$R^2$ is α-H, β-OH (except where X=CN) or =O; and $R^3$ is H.

Group II. Compounds in this group have binding affinity for the glucocorticoid receptor and generally possess antiglucocorticoid activity. These compounds [(II) wherein Z has partial structure (III)] are characterized by the following substituents:

R is H or lower acyl and in particular acetyl, propionyl, and butyryl;

$R^1$ is methyl or ethyl; and $R^2$ is α-H and an 11β-substituent as hereinabove defined containing N or S in the molecule except when X=—C≡CH. Preferred substituents are selected from the group consisting of:

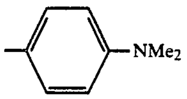 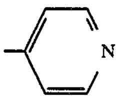

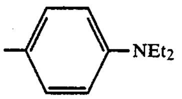 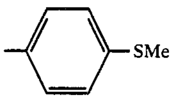

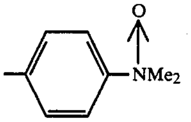 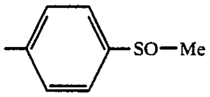

Of the 17α-methyl substituents in Group II —$OCH_3$ and $N_3$ are preferred, and $N_3$ is most preferred.

Group III. Compounds of this group have binding affinity for the progesterone receptor and generally possess progestational activity. These compounds [II; wherein Z has partial structure (III)] are characterized by substituents selected from the following:

R is H or lower acyl and in particular acetyl, propionyl, and butyryl;

$R^1$ is methyl or ethyl;

$R^2$ is α-H and β is lower alkyl such as, for example, methyl, ethyl, and n-propyl;

$R^2$ is α-H and β is lower alkenyl such as, for example, methylene, vinyl, propenyl, allyl, and isopropenyl;

$R^2$ is α-H and β is aryl such as, for example, phenyl, p-methoxyphenyl, p-fluorophenyl, and trifluoromethylphenyl;

$R^2$ is α-H, β-thienyl;

$R^2$ is α-H, β-trifluoromethyl; and $R^3$ is H or methyl.

Of the 17α-methyl substituents in Group III, —CN, —$OCH_3$ and —$N_3$ are preferred. Of these, —$OCH_3$ and —$N_3$ are more preferred.

Group IV. Compounds of this group have binding affinity for the progesterone receptor and generally posess antiprogestational activity. These compounds [II; wherein Z has partial structure (III)], are characterized by the following substituents:

R is H or lower acyl and in particular acetyl, propionyl and butyryl;

$R^1$ is methyl or ethyl;

$R^2$ is α-H and an 11β substituent as hereinabove defined containing N or S in the molecule except when X=—C≡CH. Preferred substituents are selected from the group consisting of:

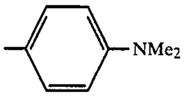 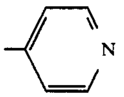

-continued

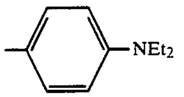 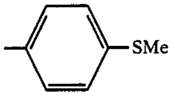

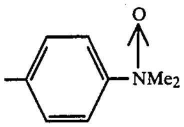 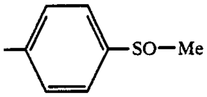

Of the 17α methyl substituents, CN is preferred.

Compounds in Groups II and IV which contain a basic center may be converted into their non-toxic, pharmaceutically acceptable acid addition salts, which are regarded as falling within the scope of the present invention. Examples of suitable acids include hydrochloric acid, sulfuric acid, phosphoric acid and organic acids such as acetic, propionic, benzoic, maleic, fumaric, succinic, tartaric, citric, lactic, toluenesulfonic, adipic, aspartic, and isethionic acid.

DESCRIPTION OF THE PREFERRED EMBODIMENTS

Figure 1:
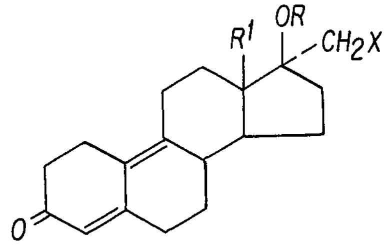
FIG. 1 shows steroid structures and partial structures I-VII which are described in greater detail herein.
Figure 1:
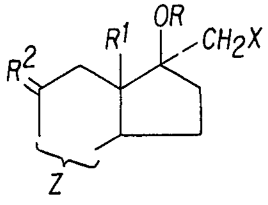
Figure 1:
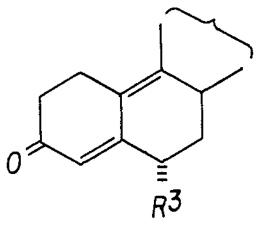
Figure 1:
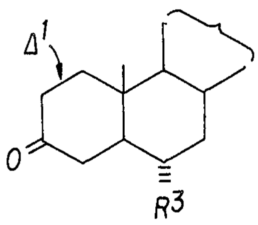
Figure 1:
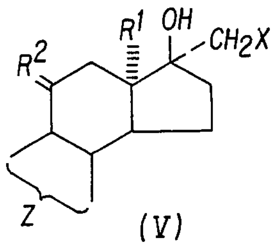
Figure 1:
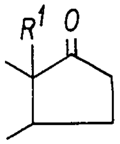
Figure 1:
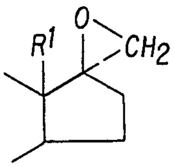
Figure 2:
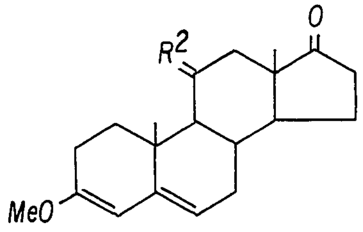
FIG. 2 shows the structures of compounds VIII-XIV which are described in greater detail herein.
Figure 2:
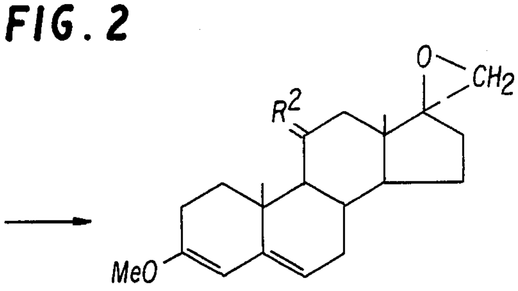
Figure 2:
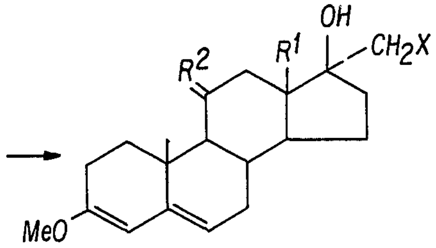
Figure 2:
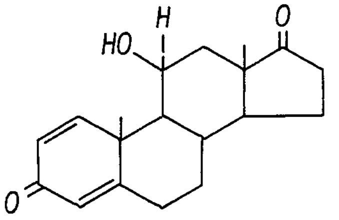
Figure 2:
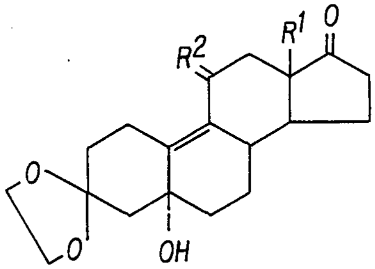
Figure 2:
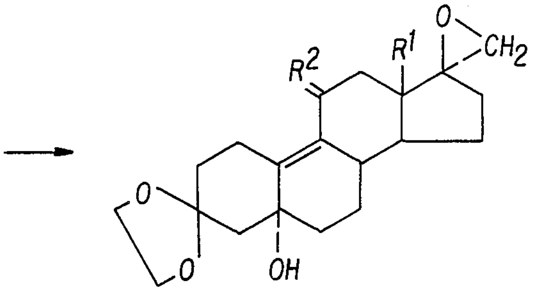
Figure 2:
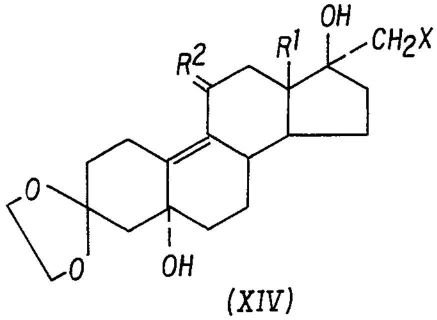

Generally, of the 17α methyl substituents, those containing a hetero atom are preferred. For example, CN, $N_3$, SCN, OMe are the methyl substituents at the 17α position which are preferred.

Specific, preferred compounds of this invention are as follows:

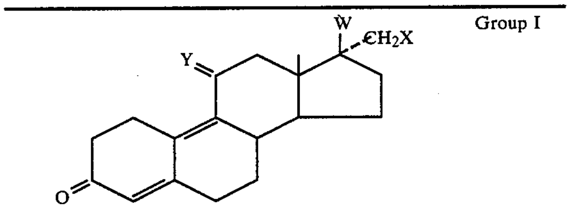

Group I

| Compound | W | X | Y |
|---|---|---|---|
| XVI | —OH | $—N_3$ | α-H,β-OH |
| XVII | —OH | $—OCH_3$ | α-H,β-OH |
| XVIII | —OH | $—N_3$ | =O |
| XIX | —OH | $—OCH_3$ | =O |

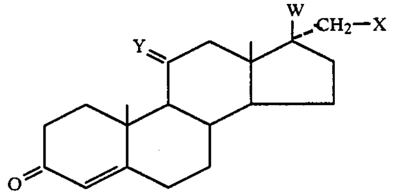

Group I

| Compound | W | X | Y | Other |
|---|---|---|---|---|
| XX | —OH | $—N_3$ | α-H,β-OH | $\Delta^1$ |
| XXI | —OH | $—OCH_3$ | α-H,β-OH | $\Delta^1$ |
| XXII | —OH | $—N_3$ | α-H,β-OH | — |
| XXIII | —OH | $—OCH_3$ | α-H,β-OH | — |
| XXIV | —OH | $—N_3$ | =O | $\Delta^1$ |
| XXV | —OH | $—OCH_3$ | =O | $\Delta^1$ |
| XXVI | —OH | $—N_3$ | =O | — |
| XXVII | —OH | $—OCH_3$ | =O | — |

-continued

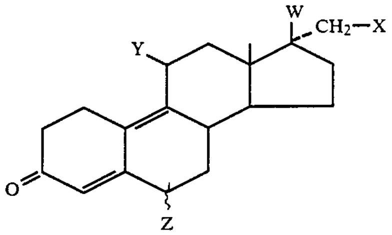

Group II and Group IV

| Compound | W | X | Y | Z |
|---|---|---|---|---|
| XVIII | —OH | —CN | 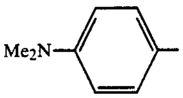 | H |
| XXIX | —OH | $—N_3$ | 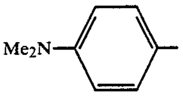 | H |
| XXX | —OH | $—OCH_3$ | 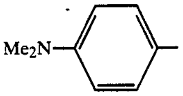 | H |
| XXXI | —OH | —CN | 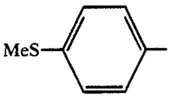 | H |
| XXXII | —OH | $—N_3$ | 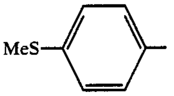 | H |
| XXXIII | —OH | $—OCH_3$ | 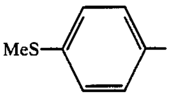 | H |
| XXXIV | —OH | —CN | 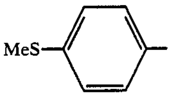 | $CH_3$ |
| XXXV | —OH | $—N_3$ | 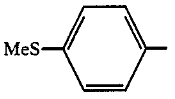 | $CH_3$ |
| XXXVI | —OH | $—OCH_3$ | 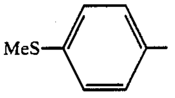 | $CH_3$ |
| XXXVII | —OH | —CN | 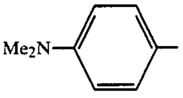 | $CH_3$ |
| XXXVIII | —OH | $—N_3$ | 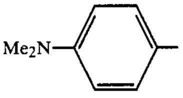 | $CH_3$ |

-continued

| | | | | |
|---|---|---|---|---|
| XXXIX | —OH | —$OCH_3$ | 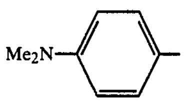 | $CH_3$ |

Group III

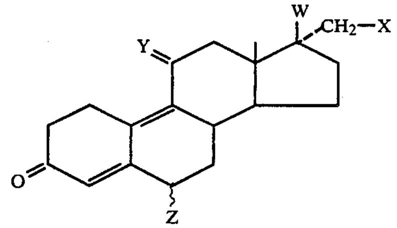

| Compound | W | X | Y | Z |
|---|---|---|---|---|
| XL | —OH | —CN | α-H,β-CH=$CH_2$ | H |
| XLI | —OH | —$N_3$ | α-H,β-CH=$CH_2$ | H |
| XLII | —OH | —$OCH_3$ | α-H,β-CH=$CH_2$ | H |
| XLIII | —OH | —C≡CH | α-H,β-CH=$CH_2$ | H |
| XLIV | —OH | —$N_3$ | α-H,β-CH=$CH_3$ | H |
| XLV | —OH | —$OCH_3$ | α-H,β-CH=$CH_3$ | H |
| XLVI | —OH | —C≡CH | α-H,β-CH=$CH_3$ | H |
| XLVII | —OH | —$N_3$ | α-H,β-CH=$CH_2$ | α-$CH_3$ |

Preparation of Compounds of the Present Invention

The compounds of the present invention are readily prepared from appropriate 17-oxo precursors of partial structure (VI) by reaction with methylide reagents such as, for example, trimethyl sulfonium iodide and sodium hydride in a solvent such as dimethylsulfoxide, to yield the oxiranes (VII) (C. E. Cook, R. C. Corley, M. E. Wall, *J. Org. Chem.* 33:2789 [1968]). The latter are then converted into the substituted methyl derivatives (II) by the method of K. Ponsold, M. Hübner, W. Schade, M. Oettel and R. Freund [*Pharmazie* 33:792 (1965)].

In preparing compounds of type (II) wherein Z=(IV), enol ethers such as (VIII) may be conveniently employed as starting materials. These compounds react readily with methylide reagents to give the oxiranes (IX) which may be converted into substituted methyl derivatives (X) by conventional methods. Dilute acid hydrolysis of (X) yields the 3-oxo-$\Delta^4$-ketones of partial structure (IV), which may be converted into $\Delta^1$-derivatives by standard procedures if so desired.

Compounds of type (II), wherein R=H, $R^1$=Me, $R^2$=α-H,β-OH and Z is represented by partial formula (IV) with a $\Delta^1$-unsaturated linkage are readily prepared from steroid (XI) which is well known in the art [G. Teutsch, G. Costerousse, R. Deraedt. J. Benzoni, M. Fortin and D. Philibert, *Steroids* 38:651-665, (1981)]. This intermediate reacts with methylide reagents to give the oxirane of partial structure (VII; $R^1$=Me). The latter can then be converted into structures [II; X is as hereinabove defined, R=H, $R^1$=Me, $R^2$=α-H,β-OH, Z is IV; $\Delta^1$)] by conventional methods as herein above defined.

In preparing compounds of type (II) wherein Z=(III), it is preferred to use the 5α-hydroxy intermediate (XII) as starting material. Compound (XII) reacts readily with methylide reagents to give the oxiranes (XIII) which may be converted into 17α-(substituted-methyl) steroids (XIV) by known methods. Mild acid hydrolysis of intermediate (XIV) results in loss of the ketal protecting group with concomitant dehydration to give structures (II) wherein Z=(III).

EXAMPLE 1

17α-Cyanomethyl-11β-(4-dimethylaminophenyl)-17β-hydroxy-4,9-estradien-3-one

Step A:

3,3-Ethylenedioxy-ξ-trimethylsilyloxy-17ξ-cyano-11β-(4-dimethylaminophenyl)-9-estren-5α-ol To a stirred suspension of magnesium (13.124 gm, 0.54 g atom) in dry tetrahydrofuran (179 ml) was added a small crystal of iodine. A solution of 4-bromo-N,N-dimethylaniline (44.72 g, 0.22 mol) and 1,2-dibromoethane (18.75 ml, 0.12 mol) in dry tetrahydrofuran (179 ml) was added at a rate to maintain reflux. Upon completion of the addition, the reaction mixture was heated at 50°-55° C. for 2.5 h, cooled to room temperature and cuprous bromide-dimethyl sulfide complex (11.54 g, 0.056 mol) was added. After the reaction mixture was stirred for an additional 30 min., more tetrahydrofuran (179 ml) was added. This was followed by addition of 3,3-ethylenedioxy-17ξ-trimethylsilyloxy-17ξ-cyano-9,11-estrene-5ξ,10ξ-epoxide (18.98 g) [J. C. Gasc and L. Nedelec, *Tetrahedron Lett.,* 2005 (1971)] in dry tetrahydrofuran (179 ml). After 2 h, the reaction mixture was poured into a vigorously stirred solution of saturated ammonium chloride (1.8 L). The phases were separated and the aqueous phase was re-extracted with ether. The crude residue (22.17 g) from the dry ether layer was partially purified by elution from silica gel 60 (200-430 mesh) using a gradient of methylene chloride/triethylamine (99.9:0.1) and methylene chloride/acetone/triethylamine (97.4:2.5:−0.1). Rechromatography using the same system gave 3.7 g of the 17β-cyano isomer and 1.78 g of the 17α-cyano isomer. β-cyano isomer: $^1$HNMR ($CDCl_3$, 60 MHz) δ 0.25 [s, $Si(CH_3)_3$], 0.55 (s, 18-$CH_3$), 2.88 [s, $N(CH_3)_2$], 3.93 [2,—O—$(CH_2)_2$—O—], 4.23 (m,11-H), 4.33 (s, 5-OH), 6.51 (d, J=9 Hz, Ar-H ortho to dimethylamino), 6.94 (d, J=9 Hz, Ar-H meta to dimethylamino); IR ($CH_2Cl_2$) 1615 (C=C), 2947 (saturated hydrocarbon), 3505 $cm^{-1}$ (5-OH); mass spectrum (70 eV) m/z (rel intensity) 550.3225 (12), 532 (100), $C_{32}H_{46}O_4N_2Si$ requires an $M^+$ at m/z 550.3226. α-cyano isomer: $^1$H NMR ($CDCl_3$, 60 MHz) δ 0.23 [s, $Si(CH_3)_3$], 0.47 (s, 18-$CH_3$), 2.85 [s, $N(CH_3)_2$], 3.90 [s,—O—$(CH_2)_2$—O—], 4.15 (s, 5-OH), 4.22 (m, 11-H), 6.52 (d, J=9 Hz, Ar-H ortho to dimethylamino), 6.93 (d, J=9 Hz, Ar-H meta to dimethylamino). IR ($CH_2Cl_2$) 1612 (C=C), 2950 (saturated hydrocarbon), 3510 $cm^{-1}$ (5-OH); mass spectrum (70 eV) m/z (rel intensity) 550.3225 (8.0), 532 (100.0).

Step B:

3,3-Ethylenedioxy-11β-(4-dimethylaminophenyl)-5α-hydroxy-9-estren-17-one

The mixture of isomers at C-17 obtained in Step A (12.4 g, 22.55 mmol) was dissolved as completely as possible in methanol (900 ml). Sodium hydroxide (10N, 100 ml) was added and the reaction mixture was stirred for 1 h at room temperature. It was then poured into distilled water (2.5 L) and the resulting precipitate extracted with methylene chloride. The methylene chloride extract was washed twice with distilled water and saturated sodium chloride and dried ($Na_2SO_4$). Solvents were flash evaporated, and the residue was dried in vacuo to afford the title ketone (7.66 g, 75.3%). $^1$H NMR ($CDCl_3$, 60 MHz) δ 0.50 (s, 18-$CH_3$), 2.87 [s, $N(CH_3)_2$], 3.92 [s,—O—$(CH_2)_2$—O—], 4.17 (m, 11-H), 4.25 (s, 5-OH), 6.50 (d, J=9 Hz, Ar-H ortho to dimethylamino), 6.93 (d, J=9 Hz, Ar-H meta to dimethylamino); IR ($CH_2Cl_2$) 1735 (17-carbonyl), 2940 (saturated hydrocarbon) and 3520 $cm^{-1}$ (5-OH); mass spectrum (70 eV) m/z (rel intensity) 451.2720 (13), 433 (100), $C_{28}H_{37}O_4N$ requires an $M^+$ at m/e 451.2722.

Step C:

3,3-Ethylenedioxy-11β-(4-dimethylaminophenyl)-spiro-17β-oxiranyl-9-estren-5α-ol

The title compound was obtained in 86% from the ketone of Step B following an analogous procedure of Cook et al. [*J. Org. Chem.* 33, 2789 (1968)]. $^1$H NMR ($CDCl_3$, 60 mHz) δ0.50 (s, 18-$CH_3$), 2.85 [s, $N(CH_3)_2$], 3.92 [2, —O—$(CH_2)_2$—O—], 4.12 (m, 11-H), 4.23 (s, 5-OH), 6.48 (d, J=9 Hz, Ar-H ortho to dimethylamino), 6.87 (d, J=9 Hz, Ar-H meta to dimethylamino); IR ($CH_2Cl_2$) 1612 (C═C), 2940 (saturated hydrocarbon), 3510 $cm^{-1}$ (5-OH); mass spectrum (70 eV) m/z (rel intensity) 465.2878 (4), 447 (36), 191 (100), $C_{29}H_{39}O_4N$ requires an $M^+$ at m/z 465.2879.

Step D:

3,3-Ethylenedioxy-11β-(4-dimethylaminophenyl)-17β-hydroxy-17α-cyanomethyl-9-estren-5α-ol The title compound was obtained in 47% yield from the oxirane of Step C following an analogous procedure to that of Wagner et al. [*J. Labelled Compd. Radiopharm.*, 17, 317 (1980)] $^1$H NMR ($CDCl_3$, 60 MHz) δ 0.52 (s, 18-$CH_3$), 2.85 [s, $N(CH_3)_2$], 3.92 [s, —O—$(CH_2)_2$—O—], 4.18 (m, 11-H), 4.28 (s, 5-OH), 6.50 (d, J=9 Hz, Ar-H ortho to dimethylamino), 6.92 (d, J=9 Hz, Ar-H meta to dimethylamino); mass spectrum (70 eV) m/z (rel intensity) 492.2985 (6), 474 (100), $C_{30}H_{40}O_4N_2$ requires an $M^+$ at m/z 492.2988.

Step E:

17α-Cyanomethyl-11β-(4-dimethylaminophenyl)-17β-hydroxy-4,9-estradien-3-one

The cyanomethyl derivative obtained in Step D (3.15 g, 6.4 mmol) was dissolved in N HCl in ethanol (75 ml) and stirred at room temperature for 2.5 h. Then the reaction mixture was poured into 500 ml of cold 5% sodium bicarbonate, and the resulting precipitate was extracted with methylene chloride. The extract was washed with distilled water and saturated sodium chloride and dried ($Na_2SO_4$). Solvents were flash evaporated, and the residue was dried in vacuo to yield 2.63 g of a pale yellow foam. The crude product was crystallized from hot methanol/ethyl acetate to yield the title compound as pale yellow crystals in 58% yield. MP (Koefler Hot Stage) around 263°-278° C. (decomposition with gas evolution and previous sweating at 235° C. and formation of moisture at 250° C.); $^1$H NMR ($CDCl_3$, 60 Hz) δ 0.58 (s, 18-$CH_3$), 2.85 [s, $N(CH_3)_2$], 4.30 (m, 11α-H), 5.67 (s, 4-H), 6.50 (d, J=9 Hz, Ar-H ortho to dimethylamino), 6.88 (d, J=9 Hz, Ar-H meta to dimethylamino); IR ($CH_2Cl_2$) 3610 (hydroxyl), 2950 (saturated hydrocarbon), 2260 (C≡N), 1660 $cm^{-1}$ (unsaturated carbonyl); mass spectrum (70 eV) m/z 430.2620 (7), 389 (60), 121 (100), $C_{28}H_{34}O_2N_2$ requires an $M^+$ at m/z 430.2620.

Anal. Calcd for $C_{28}H_{30}O_2N_2$: C, 78.10; H, 7.96; N, 6.51. Found: C, 78.03; H, 8.00; N, 6.48.

EXAMPLE 2

11β-(4-Dimethylaminophenyl)-17β-hydroxy-17α-azidomethyl-4,9-estradien-3-one

A solution of the oxirane obtained in Step C, Example 1, (150 mg, 0.32 mmol) and sodium azide (300 mg, 4.62 mmol) in methanol (3 ml) was refluxed for 6 h. The reaction mixture was then cooled to room temperature and treated with 4 ml of 1N HCl in ethanol. After 45 min, the reaction mixture was added to 5% sodium bicarbonate and extracted with methylene chloride. After the extract was washed with water and saturated sodium chloride solution, it was dried ($Na_2SO_4$) and the solvent evaporated. The resulting residue was purified by preparative thin layer chromatography on silica gel 60 F-254 developed with ethyl acetate/triethylamine (99.5:0.5) to yield 31.8 mg (22.1%) of the title compound: $^1$H NMR (250 MHz, $CDCl_3$), δ 0.60 (s, 3, 18-$CH_3$), 2.92 (d, 6, J=0.89 Hz, $CH_3$—N—$CH_3$), 3.27 (d, 1, J=12.1 Hz, CH—$N_3$), 3.58 (d, 1, J=12.1 Hz, CH—$N_3$), 4.34 [m (appears as d separated by 6.5 Hz), 1, 11-H], 5.76 (s, 1, 4-H), 6.66 (d, 2, J=8.5 Hz, Ar-H ortho to $CH_3$—N—$CH_3$, 7.01 (d, 2, J=8.5 Hz, Ar-H); mass spectrum (70 eV), m/z (rel intensity) 446.2681 (33.0), 418 (24.0), 389 (19.1), 121 (100.0), $C_{27}H_{34}N_4O_2$ requires an $M^+$ at m/z 446.2681.

EXAMPLE 3

11β-(4-Dimethylaminophenyl)-17β-hydroxy-17α-methoxymethyl-4,9-estradien-3-one

A solution of the oxirane of Step C, Example 1, (25 mg, 0.054 mmol) and sodium hydroxide (25 mg) in methanol (1 ml) was stirred at 50°-55° C. for 24 h. An additional 50 mg of sodium hydroxide was then added and heating was continued for a total of 48 h. The reaction mixture was diluted with distilled water, and the resulting precipitate was extracted with methylene chloride. After the extract was washed with water (3×) and saturated sodium chloride solution, it was dried ($Na_2SO_4$) and the solvent was evaporated. The resulting residue was stirred with N HCl in ethanol (1 ml) for 45 min at room temperature, neutralized with aqueous sodium bicarbonate and extracted with methylene chloride. The residue from the dry methylene chloride layer was purified by reverse phase chromatography using a Lobar ® RP-8 column equilibrated with 20% water in methanol to give the title compound: $^1$H NMR (250 MHz, $CDCl_3$), δ 0.58 (s, 3, 18-$CH_3$), 2.91 (s, 6, $CH_3$—N—$CH_3$), 3.21 (d, 1, J=9.1 Hz, CH—$OCH_3$), 3.41 (s, 3, $OCH_3$), 3.55 (d, 1, J=9.1 Hz, CH—$OCH_3$), 4.31 [m, (appears as d separated by 6.6 Hz), 1, 11-H], 5.75 (s, 1, 4-H), 6.65 (d, 2, J=8.7 Hz, Ar-H ortho to $CH_3$—N—$CH_3$), 7.02 (d, 2, J=8.7 Hz, Ar-H); mass spectrum (70 eV) m/z (rel intensity), 435.2774 (72.4), 280 (11.7), 134 (24.1), 121 (100.0), $C_{28}H_{37}N_1O_3$ requires $M^+$ at m/z 435.2773.

EXAMPLE 4

11β-(4-Dimethylaminophenyl)-17β-hydroxy-17α-benzyl-4,9-estradien-3-one

Boron trifluoride etherate (0.75 ml) was added in a dry atmosphere to a solution of phenyl lithium (3.0 ml of a 1.7M solution in ethyl ether/cyclohexane 7:3) in tetrahydrofuran (10 ml) at −78° C. After the reaction mixture was stirred for 10 min, the oxirane of Step C, Example 1, (125 mg) in tetrahydrofuran (5 ml) was added dropwise over 2 min. After 1 h more boron trifluoride etherate (0.75 ml) was added. Two hours later the reaction mixture was poured cautiously into cold saturated ammonium chloride. The resulting solution was stirred vigorously for 30 min at room temperature and then was extracted with methylene chloride. After the extract was washed with water and saturated sodium chloride solution, it was dried ($Na_2SO_4$) and solvents were evaporated. The resulting residue was chromatographed on a size B (E. Merck) Lobar® RP-8 column (10% $H_2O$ in methanol) to afford 68 mg (52.7%) of the title compound. $^1H$ NMR ($CDCl_3$, 250 MHz) δ 0.65 (s, 3, 18-$CH_3$), δ 2.37 (m, H-C-ϕ), 2.62 (m, H-C-ϕ), 2.92 (s, 6, $CH_3$—N—$CH_3$), 4.41 (apparent d, 1, 11-H), 5.78 (s, 1, 4-H), 6.67 (d, 2, J=8.7, Ar-H ortho to $CH_3$—N—$CH_3$), 7.06 (d, 2, J=8.7, Ar-H meta to $CH_3$—N—$CH_3$), 7.25–7.35 (m, 4, remaining aromatic protons).

EXAMPLE 5

11β-(4-Dimethylaminophenyl)-17β-hydroxy-17α-prop-2-yn-1-yl-4,9-estradien-3-one Under anhydrous reaction conditions in a nitrogen atmosphere, pure acetylene was bubbled for 20 min at −78° C. into tetrahydrofuran (2 ml) containing 0.65 ml of 1.5M n-butyllithium in hexane. Boron trifluoride etherate (0.15 ml) was added and the reaction mixture was stirred for 10 min at −78° C. Then oxirane of Step C, Example 1, (25 mg. 0.054 mmol), dissolved in tetrahydrofuran (2 ml) was added under stirring [cf. M. Yamaguchi and I. Hirao, *Tetrahedron Lett.*, 24, 391 (1983)]. After 1 h, more boron trifluoride etherate (0.15 ml) was added. Two hours later the reaction mixture was poured *cautiously* into cold saturated ammonium chloride. The resulting solution was stirred vigorously for 15 min at room temperature and then was extracted with ether. The aqueous phase was basified to pH 9–10 and was extracted with ether. This extract was washed with distilled water until the wash was neutral and then once with saturated sodium chloride solution and dried ($Na_2SO_4$). Solvents were removed by flash evaporation. The resulting residue was purified by preparative thin layer chromatography on a silica gel plate (20×20×0.25 cm, E. Merck) developed with acetone/methylene chloride (2:8) containing a few drops of triethylamine (5 mg, 21.7%). Mass spectrum (70 eV) m/z (rel intensitly) 429.2669 (16.0), 293 (10.7), 149 (100.0), $C_{29}H_{35}NO_2$ requires an M+ at m/z 429.2668; $^1H$ NMR ($CDCl_3$, 250 MHz), δ 0.62 (s, 3, 18-$CH_3$), 2.37 (s, possibly C≡CH), 2.92 (2, 6, $CH_3$—N—$CH_3$), 4.35 [m (appears as d separated by 6.8 Hz), 1, 11-H], 5.76 (s, 1, 4-H), 6.66 (d, 2, J=8.8, Ar-H ortho to $CH_3$—N—$CH_3$), 7.01 (d, 2, J=8.8, Ar-H).

EXAMPLE 6

The compounds corresponding to the products of Examples 1(E), 2, 3, 4 and 5 in which the 11β-substituent is methyl instead of 4-N,N-dimethylaminophenyl-are synthesized from the known 3,3-ethylenedioxy-17ξ-trimethylsilyloxy-17ξ-cyano-11β-methyl-9-estren-5α-ol [G. Teutsch, *Tetrahedron Lett.*, 23, 4697 (1982)] using the procedures described in Examples 1B–E, 2, 3, 4 and 5.

EXAMPLE 7

17α-Azidomethyl-11β-(4-dimethylaminophenyl)-11β,17β-dihydroxyandrost-1,4-dien-3-one The title compound is synthesized from 11β-androsta-1,4-diene-3,17-dione by successive application of the methods of Example 1, Step C and Example 2.

Activity

EXAMPLE 8

The in vitro activity of the subject compounds was determined by measuring the binding affinities (RBA) of these compounds relative to progesterone for the progesterone receptor in the cytosol obtained from estrogen-primed immature rabbit uterus, by measuring the RBA relative to dexamethasone for the glucocorticoid receptor from thymus of adrenalectomized rats and by measuring the RBA relative to estradiol for the estrogen receptor from immature rat uterus. These assays were carried out by the procedures of J. R. Reel et al., *Fertility and Sterility,* 31, 552 (1979) (progesterone), G. P. Chrousos et al., *Endocrinology,* 107, 472 (1980) (glucocorticoid), and S. G. Korenman et al, *J. Clin. Endocrinol.,* 28, 127 (1968) (estrogen). The results are presented in Table 1. RBA values greater than 100 indicate a higher affinity for the receptor than the steroid used as standard. Thus, compounds XVa–XVe have affinity for the progestin receptor with RBA's about half that of the natural hormone progesterone. In some cases, especially XVc and XVd, this is accompanied by very strong binding to the glucocorticoid receptor (ca. 3 times the RBA of the potent corticosteroid dexamethasone). The compounds do not bind to the estrogen receptor and thus appear devoid of inherent estrogenic activity.

The strong binding to the glucocorticoid receptor is in surprising contrast to the findings of H. Hoffmann et al. [*Exper. Clin. Endocrinol.* 81, 146 (1983)] that the simpler compound Ia did not show any glucocorticoid or antiexudative properties and thus illustrates the surprising range of biological activities encompassed by the present series of compounds compared to the prior art.

EXAMPLE 9

In vivo Antiprogestational Activity

The antiprogestational activity of compound XVa was studied after both intrauterine and oral administration. In each case the compound was tested for its ability to inhibit the endometrial response due to subcutaneous administration of progesterone to estrogen-primed immature female rabbits. The methodology used for the intrauterine test has been described by D. A. McGinty et al [*Endocrinology,* 24, 829 (1939)]. For oral administration of test compounds the method used was analogous to that of Clauberg [Clauberg, *Zentr. Gynakol,* 54, 2757 (1930)] as modified by McPhail [*J. Physiol.* (*London*) 83, 145 (1935)].

The results of these tests are given in Table 2. They show a clear, dose-related antiprogestational effect. This is again in contrast to the results found by S. Stölzner et al. [*Exper. Clin. Endocrinol.,* 81, 115 (1983)] on the simpler analog I (STS 557) which had strong progestational activity. It shows the striking influence of the 11-substituent on biological activity of the subject compounds.

TABLE 1

| BINDING AFFINITIES OF COMPOUNDS XVa-XVe FOR PROGESTERONE, GLUCOCORTICOID, AND ESTROGEN RECEPTORS[a] | | | |
|---|---|---|---|
| | RBA[b] for Receptors | | |
| Compound | Progestin | Glucocorticoid | Estrogen |
| Progesterone | 100 | 24 | 0 |
| Dexamethasone | 0.1 | 100 | 0 |
| Estradiol | — | — | 100 |
| XVa | 33 | 74 | 0 |
| XVb | 71 | 143 | 0 |
| XVc | 54 | 413 | 0 |
| XVd | 64 | 274 | 0 |
| XVe | 23 | 100 | 0 |

[a]The test procedure involved incubation of test compound (varied concentrations) with cytosol containing the receptor and a tritium-labeled ligand (progesterone, dexamethasone or estradiol). The concentration required to displace 50% of bound radioligand is determined graphically and compared with that of an unlabeled standard (progesterone, dexamethasone or estradiol).
[b]These results are the average of 1-3 assays.

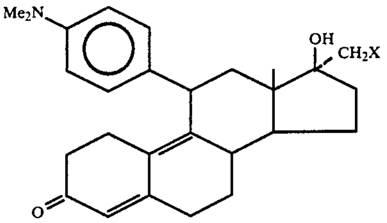

a. X = CN
b. X = C≡CH
c. X = $N_3$
d. X = $OCH_3$
e. X = $C_6H_5$

XV

TABLE 2

| ANTIPROGESTATIONAL ACTIVITY OF XVa[a] | | | |
|---|---|---|---|
| Compound | Route | Total Dose per Rabbit | % Inhibition of Progestational Response |
| XVa | Intrauterine | 0 | 0 |
| | Intrauterine | 1.0 μg | 7.3 ± 4.5 |
| | Intrauterine | 5.0 μg | 26.7 ± 4.5 |
| | Intrauterine | 10.0 μg | 80.5 ± 9.8 |
| | Intrauterine | 40.0 μg | 96.3 ± 3.7 |
| XVa | Oral | 0 | 0 |
| | Oral | 5 mg | 7.8 ± 6.0 |
| | Oral | 10 mg | 56.2 ± 7.1 |
| | Oral | 20 mg | 79.1 ± 7.4 |

[a]Immature female rabbits are primed with estrogen and dosed with progesterone (subcutaneous, 0.8 mg total dose). Uterine tissue is fixed, stained and scored for endometrial proliferation according to McPhail.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including silastic and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredients in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The compounds of this invention may also be administered in the form of suppositories for rectal administraton of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

They may also be administered by intranasal, intraocular, intravaginal, and intrarectal routes including suppositories, insufflation, powders and aerosol formulation.

Products of the invention which are preferably administered by the topical route, and in particular those of Group I, may be administered as applicator sticks, solutions, suspensions, emulsions, gels, creams, ointments, pastes, jellies, paints, powders, and aerosols.

Products falling within Group I are of particular utility as topical glucocorticoids of value in the treatment of inflammatory, allergic and other skin conditions, both alone and in combination with an antibiotic such as neomycin. Products falling within Group II are of particular value in pathological conditions characterized by excess endogenous glucocorticoids such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products falling within Group III are of particular value as progestational agents, ovulation inhibitors, menses regulators, contraceptive agents, agents for synchronization of fertile periods in cattle, endometriosis, and the like. When used for contraceptive purposes, they may conveniently be admixed with estrogenic agents, such for example as ethynylestradiol or estradiol esters.

Products falling within Group IV are characterized by antagonizing the effects of progesterone. As such, they are of particular value in control of hormonal irregularities in the menstrual cycle and for synchronization of fertile periods in cattle. They may also be administered in conjunction with prostaglandins, oxytocics, zoapatanol and the like.

The compounds of the invention may be used for control of fertility during the whole of the reproductive cycle. They are of particular value as postcoital contraceptives, for rendering the uterus inimical to implantation, and as "once a month" contraceptive agents. They may also be used in conjuction with prostaglandins, oxytocics and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to progestational and/or anti-progestational agents. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the host treated and the particular mode of administration. For example, a unit dose of the steroid may preferably contain betweeen 0.0001 grams and 1 gram of the active ingredient. A more preferred unit dose is betwen 0.001 and 0.1 grams. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A steroid having binding affinity for the glucocorticoid receptor and possessing glucocorticoid activity, selected from the group represented by partial formula (II), wherein Z is selected from partial structures (III) or (IV),

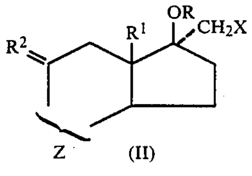

(II)

-continued

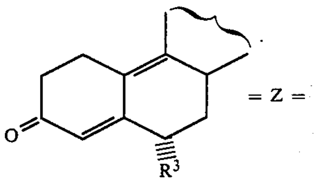

(III)

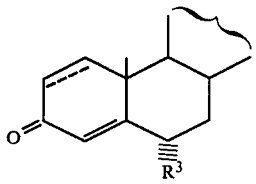

(IV)

wherein:
- X is selected from the group consisting of —C≡CH, CN, $N_3$, SCN, OMe, and Ph;
- R is acetyl, propionyl or butyryl;
- $R^1$ is methyl;
- $R^2$ is α-H, β-OH or =O, with the proviso that when X is CN, $R^2$ is =O; and
- $R^3$ is H.

2. A steroid according to claim 1, wherein X is CN, $N_3$ or OMe.

3. A method of inducing a glucocorticoid hormonal response, which comprises administering an effective amount of a steroid according to claim 1, to a warm-blooded mammal in need thereof.

4. The method of claim 3, wherein said warm-blooded mammal is a primate, domestic pet or farm animal.

5. The method of claim 3, wherein the unit dose of the steroid lies between 0.0001 grams and 1.0 gram.

6. A steroid having binding affinity for the glucocorticoid receptor and possessing antiglucocorticoid activity, selected from the group represented by partial formula II, wherein Z has partial structure III,

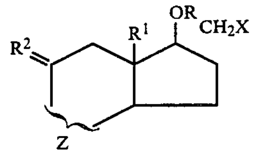

(II)

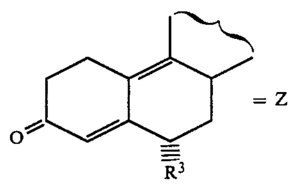

(III)

wherein:
- X is selected from the group consisting of $N_3$, SCN, and Ph;
- R is H or $C_1$–$C_5$ acyl;
- $R^1$ is methyl or ethyl;
- $R^2$ is α-H and an 11β-substituent selected from the group consisting of:
- (A) $—(CH_2)_nR^5$ wherein $n \leqq 4$ and $R^5$=pyridyl, thiazolyl, $—NMe_2$, $—NEt_2$,

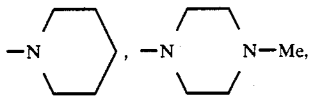

OMe;
- (B) $—C_6H_4.R^4$ wherein $R^4$ is selected from among the substituents in $R^5$ or wherein $R^4$=—H, $—OCH_2CH_2NMe_2$, $—OCH_2CH_2NEt_2$, or —O—($C_1$–$C_3$) alkyl;
- (C) -halogen, —S—($C_1$–$C_3$) alkyl, —S(O)—($C_1$–$C_3$) alkyl;
- (D) -S-phenyl, or —S(O)-phenyl;

or $R^2$ is α-H, β-$CF_3$; α-H, β-$CHF_2$; =CHF; or $—CF_2$ and $R_3$ is H or $CH_3$.

7. A steroid according to claim 6, wherein $R^2$ is α-H and an 11β-substituent selected from the group consisting of:

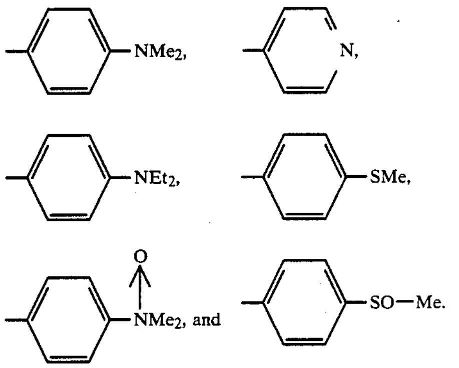

8. A steroid according to claim 6, wherein R is acetyl, propionyl or butyryl.

9. A method of inducing an anti-glucocorticoid antihormonal response, which comprises administering an effective amount of a steroid of claim 6, to a warm-blooded mammal in need thereof.

10. The method of claim 9, wherein said warm-blooded mammal is a primate, domestic pet or farm animal.

11. The method of claim 9 wherein the unit dose of the steroid lies between 0.0001 grams and 1.0 gram.

12. A steroid having binding affinity for the progesterone receptor and possessing antiprogestational activity, selected from the group represented by partial formula II, wherein Z has partial structure III,

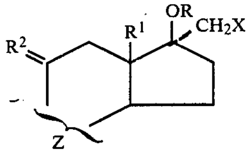

(II)

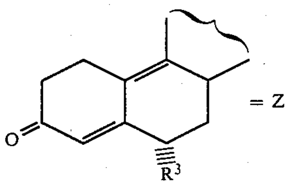

(III)

wherein:

X is selected from the group consisting of $N_3$; SCN; and Ph;

R is H or lower acyl;

$R^1$ is methyl or ethyl;

$R^2$ is $\alpha$-H and an $11\beta$-substituent selected from the group consisting of:

(A) —$(CH_2)_nR^5$ wherein $n \leqq 4$ and $R^5$=pyridyl, thiazolyl, —$NMe_2$, —$NEt_2$,

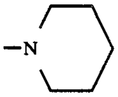, 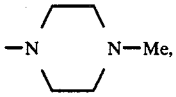

—OMe;

(B) —$C_6H_4.R^4$ wherein $R^4$ is selected from among the substituents in $R^5$ or wherein $R^4$=—H, —$OCH_2CH_2NMe_2$, —$OCH_2CH_2NEt_2$, or —O—($C_1$-$C_3$) alkyl;

(C) -halogen, —S—($C_1$-$C_3$) alkyl, —S(O)—($C_1$-$C_3$) alkyl;

(D) -S-phenyl, or —S(O)-phenyl; or $R^2$ is $\alpha$-H, $\beta$-$CHF_2$; =CHF or =$CF_2$ and $R^3$ is H or $CH_3$.

13. A steroid according to claim 12, wherein $R^2$ is $\alpha$-H and an $11\beta$-substituent selected from the group consisting of:

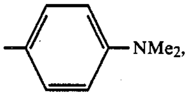 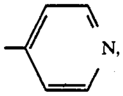

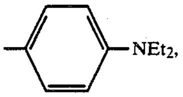 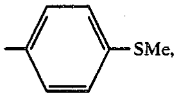

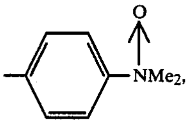 and 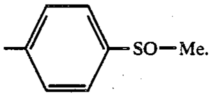

14. A steroid according to claim 12, wherein R is acetyl, propionyl, or butyryl.

15. A method of inducing an anti-progestational antihormonal response, which comprises administering an effective amount of a steroid of claim 12 to a warm-blooded mammal in need thereof.

16. The method of claim 15, wherein said warm-blooded mammal is a primate, domestic pet or farm animal.

17. The method of claim 15, wherein the unit dose of the steroid lies between 0.0001 grams and 1.0 gram.

* * * * *

UNITED STATES PATENT AND TRADEMARK OFFICE
CERTIFICATE OF CORRECTION

PATENT NO. : 4,774,236

DATED : SEPTEMBER 27, 1988

INVENTOR(S) : C. EDGAR COOK ET AL

It is certified that error appears in the above-identified patent and that said Letters Patent is hereby corrected as shown below:

In the ABSTRACT, in the first portion of the formula, delete

" 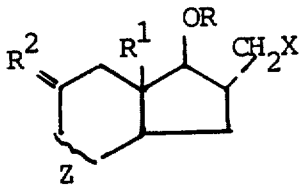 ", and insert -- 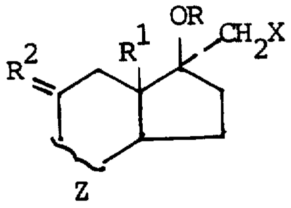 --.

In the Claims, Claim 6, lines 45-50, Structure II, delete

" 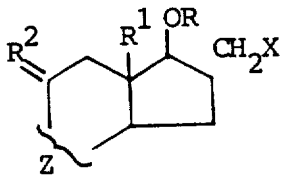 ", and insert -- 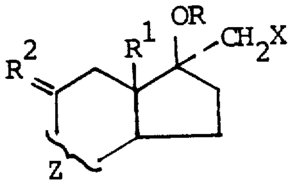 --;

Claim 12, lines 55-60, Structure II, delete

" 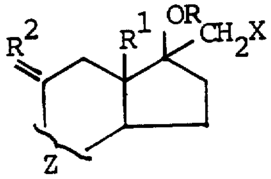 ", and insert -- 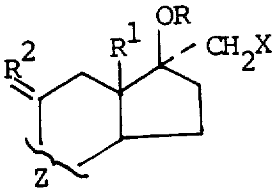 --.

Signed and Sealed this

First Day of August, 1989

*Attest:*

DONALD J. QUIGG

*Attesting Officer* *Commissioner of Patents and Trademarks*